United States Patent
Whelan et al.

(10) Patent No.: US 7,551,957 B2
(45) Date of Patent: Jun. 23, 2009

(54) ELECTROMAGNETIC THERAPY DEVICE AND METHODS

(75) Inventors: Andrew J. Whelan, Frederick, MD (US); John Martinez, Houston, TX (US); Timothy Cox, Friendswood, TX (US); Stephanie Toy, League City, TX (US); James Woodhams, Escondido, CA (US)

(73) Assignee: BioElectronics Corp., Frederick, MD (US)

( * ) Notice: Subject to any disclaimer, the term of this patent is extended or adjusted under 35 U.S.C. 154(b) by 0 days.

(21) Appl. No.: 10/384,101

(22) Filed: Mar. 6, 2003

(65) Prior Publication Data

US 2004/0176803 A1 Sep. 9, 2004

(51) Int. Cl.
*A61N 1/00* (2006.01)
(52) U.S. Cl. .......................................................... 607/2
(58) Field of Classification Search ....................... 607/2, 607/50; 604/20; 374/209; 600/407; 323/284; 340/5.61, 573.4; 368/12; 310/254; 318/696; 345/169
See application file for complete search history.

(56) References Cited

U.S. PATENT DOCUMENTS

| | | | |
|---|---|---|---|
| 3,769,575 A | 10/1973 | Rist et al. | |
| 4,007,832 A * | 2/1977 | Paull et al. | 374/209 |
| 4,144,706 A * | 3/1979 | Willis | 368/12 |
| 4,412,540 A | 11/1983 | Bentall | |
| 4,429,698 A | 2/1984 | Bentall | |
| 4,471,787 A | 9/1984 | Bentall | |
| 4,576,172 A | 3/1986 | Bentall | |
| 4,611,599 A | 9/1986 | Bentall et al. | |
| 4,801,459 A * | 1/1989 | Liburdy | 604/2 |
| 4,850,372 A | 7/1989 | Ko et al. | |
| 4,853,682 A * | 8/1989 | Asano et al. | 345/169 |
| 4,942,884 A | 7/1990 | Ichinomiya et al. | |
| 4,998,532 A * | 3/1991 | Griffith | 607/2 |
| 5,218,344 A * | 6/1993 | Ricketts | 340/573.4 |
| 5,441,528 A | 8/1995 | Chang et al. | 607/69 |
| 5,478,303 A | 12/1995 | Foley-Nolan et al. | |
| 5,792,209 A | 8/1998 | Varner | 607/51 |
| 5,814,979 A * | 9/1998 | Grimm | 323/284 |
| 5,951,459 A | 9/1999 | Blackwell | 600/13 |
| 6,317,630 B1 | 11/2001 | Gross et al. | |
| 6,332,087 B1 * | 12/2001 | Svenson et al. | 600/407 |
| 6,334,069 B1 | 12/2001 | George et al. | |
| 6,445,955 B1 | 9/2002 | Michelson et al. | 607/46 |
| 6,463,336 B1 | 10/2002 | Mawhinney | 607/156 |
| 6,476,579 B1 * | 11/2002 | Akahane et al. | 318/696 |
| 6,603,236 B2 * | 8/2003 | Nagasaka | 310/254 |
| 6,701,185 B2 | 3/2004 | Burnett et al. | 607/2 |
| 6,825,751 B1 * | 11/2004 | Kita et al. | 340/5.61 |

OTHER PUBLICATIONS

*Sports Injury Advisor*, Data sheet [on-line] Retrieved from the Internet Jul. 2, 2003 at URL: http://www.sportsinjuryadvisor.com.

* cited by examiner

*Primary Examiner*—George Manuel
(74) *Attorney, Agent, or Firm*—Fish & Richardson P.C.

(57) ABSTRACT

Systems and techniques for applying an electromagnetic field to bodily tissue include a self-contained and portable electromagnetic field generating device disposed over a surface of bodily tissue such that the radiated electromagnetic fields impinge upon the bodily tissue. The device includes an electromagnetic field generator, which is coupled to an antenna that is arranged to radiate the electromagnetic field. A power source is coupled to the generator to provide power for the device and an activator is used to initiate radiation of the electromagnetic field.

14 Claims, 5 Drawing Sheets

ELECTROMAGNETIC THERAPY DEVICE AND METHODS

BACKGROUND

The following description relates to an electromagnetic field radiator that influences the metabolic characteristics of living systems. The techniques may be used to therapeutically promote healing of tissue and treat diseases.

Therapeutic value may be achieved by applying an electromagnetic field to injured bodily tissue. Application of a high-frequency electromagnetic field at a sufficiently low field strength so as not to produce tissue heating may result in a beneficial effect on healing of the tissue.

In some cases effectiveness of the therapeutic effect of the electromagnetic field may be improved by extending the duration of application of the field. The power requirements of the applied field may be reduced and the effectiveness of the treatment increased by extending the treatment duration.

SUMMARY OF THE DISCLOSURE

The present application teaches systems and techniques for applying an electromagnetic field to bodily tissue.

In one aspect, a device for applying a therapeutic electromagnetic field is disclosed including an electromagnetic field generator, which is coupled to an antenna that is arranged to radiate the electromagnetic field. A power source is coupled to the generator to provide power for the device and an activator is used to initiate radiation of the electromagnetic field. The therapeutic device is self-contained and portable and is disposed over a surface of bodily tissue such that the radiated electromagnetic field impinges upon the bodily tissue.

In an implementation, the power source is a battery of less than approximately 10 VDC.

In another implementation, the device is a component of a therapeutic delivery system. The therapeutic delivery system includes a member from the group of a patch, a bandage, a pad, a brace, a strap, tape, adhesive and a cast.

In another aspect, a technique for applying a therapeutic electromagnetic field is facilitated by incorporating a power source, antenna and electromagnetic field generator within a portable and disposable package and affixing the device to bodily tissue. The device generates an electromagnetic field that induces an alternating current in the bodily tissue.

In another implementation, the average available radiated power is less than approximately 1 milliwatt and the peak available radiated power density is less than 100 microwatts per square centimeter measured substantially at the surface of the tissue.

Some implementations of the systems and techniques described herein may provide one or more of the following advantages. The device may be suitable for prolonged use. The self-contained unit can encourage patient compliance. In some implementations the device may be placed directly over bodily tissue to provide electromagnetic therapy to the tissue. The device may be part of a therapeutic agent delivery system such as a patch, bandage, pad, brace, cast, or other tissue injury support device.

Details of one or more implementations are set forth in the accompanying drawings and the description below. Other features and advantages will be apparent from the description and drawings, and from the claims.

BRIEF DESCRIPTION OF DRAWINGS

Like reference symbols in the various drawings indicate like elements.

DETAILED DESCRIPTION

The systems and techniques described here relate to promoting therapeutic healing of tissue, providing prophylaxis for, and treatment of disorders and diseases through the application of an electromagnetic field. The techniques include providing a self-contained miniaturized electromagnetic field generating device that may be applied to bodily tissue. In some implementations the techniques and systems include devices that are disposable and portable.

These techniques also may provide a method of transmission and utilization of the body's capacitance by affixing a transmitting element of the device to conform and fit closely over the bodily tissue, provide a small space and low weight device for field transport and emergency use. Patient compliance with a therapeutic regimen may be important to promote healing of bodily tissue. Patient compliance may be improved by providing a therapeutic device that is self-contained and portable.

Some or all of the components of a therapeutic electromagnetic energy delivery device may be integrated into a control circuit chip to miniaturize the device. The device may be affixed to various parts of the body for prolonged electromagnetic therapy. Patient compliance to the therapeutic regimen may be improved by embedding or concealing the device into a patch, bandage, pad, wrap, brace, cast, or other injury support device and affixed to the body or taped over the bodily tissue.

The effectiveness of electromagnetic therapy may be improved by extending the treatment duration. Lower power electromagnetic radiation may be applied for a longer period of time than may be necessary for shorter periods of application. The self-contained unit disclosed may promote patient compliance with periods of therapy that may extend over weeks.

Figure 1:
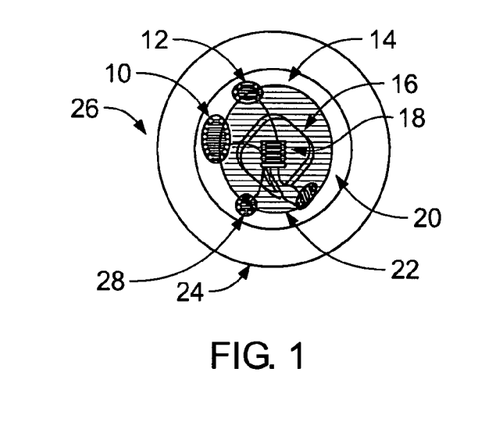
FIG. 1 is an implementation of a therapeutic electromagnetic device depicting an arrangement of the components.

FIG. 1 illustrates an implementation of a therapeutic electromagnetic device 26. A control circuit chip 18 may provide the functionality for the therapeutic electromagnetic device to operate. An implementation of a control chip 18 is disclosed in association with the description of FIG. 3 and includes a radio frequency (RF) generator. A power source 10 coupled directly or indirectly to the control chip may be used to power the therapeutic electromagnetic device. The power source may include a battery, photovoltaic cell or an electro-chemical cell. An activator 12 is used to activate the device. The activator may include a switch that is a single-use or multiple use type and may be momentary or alternate-action. Actuation of the activator may be accomplished in various ways including by use of pressure, light or electronic signal either remotely or proximately. An antenna 16 is used to emit electromagnetic radiation and a deflector shield 14 may be used to deflect the electromagnetic radiation to the bodily tissue. In an implementation, the antenna 16 and/or deflector 14 may be tuned for electromagnetic energy in the frequency range of 27+/0.5 Mhz. The therapeutic electromagnetic device also may include a tuning coil 20 which may be used to match the impedance of the antenna 16 to the RF signal generator within the control circuit chip 18. A circuit board 22 may be used to mount the elements of the device and, in some cases, provide coupling between the elements of the device. The circuit board may be comprised of a rigid or flexible material. The assembled device weighs less than 12 grams.

In some implementations, an adhesive material 24 may be used for affixing the therapeutic electromagnetic device to bodily tissue. Adhesive material 24 includes, for example, pharmaceutical grade adhesives. The therapeutic electromagnetic device may be affixed using other single or multiple usage therapeutic delivery devices, which include a patch, a bandage, a pad, a brace, a strap, tape, adhesive and a cast. In some implementations, an indicator 28 can be used to provide indicia that the therapeutic electromagnetic device is active. The indicator 28 may include one or more of the following: a visual indicator such as a light emitting diode (LED), lamp or electro-luminescent display; an auditory indicator such as noise generator; or a tactile indicator such as a vibrator. In an implementation, the indicator may be coupled to an electromagnetic field detector in the control circuit chip 18 and indicate the presence or lack of electromagnetic radiation from the device. In various implementations the indicator may be steady, intermittent or pulsed.

The therapeutic electromagnetic device may be enclosed or encapsulated in encapsulants or other potting compounds to reduce the vulnerability of the device to foreign materials including moisture, fluids, fungus, static charges, dirt, particulate matter and dust. The encapsulants, including insulating resins such as epoxies, polyurethanes, and polyesters, may be cast into cavities containing the device components, to insulate, protect, and hold the components in place. The encapsulant also may reduce the vulnerability of the device to environmental factors including air, heat, sunlight, ultraviolet light and spurious electromagnetic fields. In some implementations, a conformal coating may be applied to the device components and couplings to reduce the vulnerability of the device to moisture, fluids, fungus, static charges, dirt, particulate matter and dust.

Figure 2:
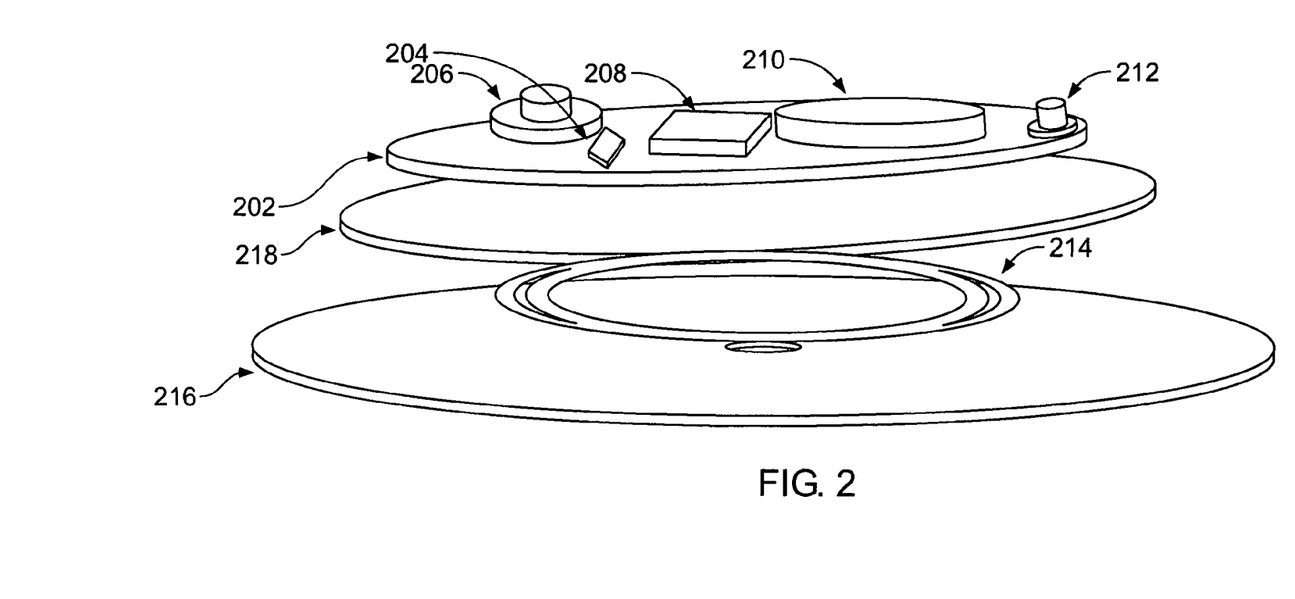
FIG. 2 is an implementation of a therapeutic electromagnetic patch depicting components in layers.
Figure 6:
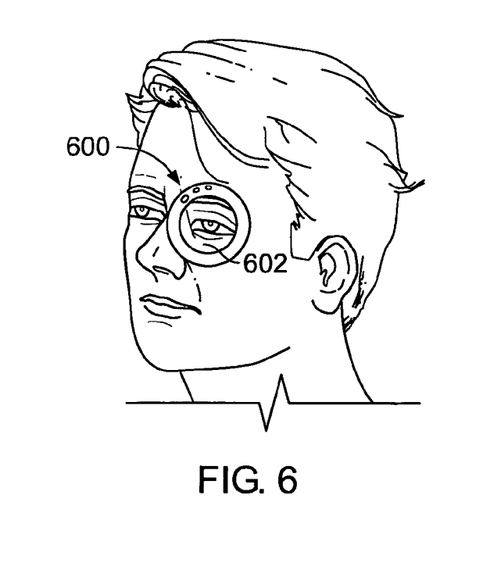
FIG. 6 depicts an alternative configuration of a therapeutic electromagnetic device.

FIG. 2 illustrates an exploded view of an implementation of the therapeutic electromagnetic device having the components in a layered form. An activation switch 206, a control circuit chip 208, a power source 210, a visual indicator 212 and a tuning coil 204 may be mounted on a top layer and attached to a circuit board 202 to provide coupling between the components. A deflecting shield 218 may be layered under the circuit board 202. In an implementation, the deflecting shield 218 may be a layer or coating of material, having high magnetic permeability, applied directly to circuit board 202. An antenna 214 to radiate electromagnetic energy may be layered under deflecting shield 218 and coupled to the circuit board 202. The deflecting shield 218 may deflect some of the energy radiated from the antenna 214 away from components mounted on the circuit board and toward the bodily tissue. The shape of the antenna is not restricted and some common shapes are depicted in FIGS. 5A-I. In some implementations, the antenna may comprise separate conductors that do not make electrical contact with each other. The induced electric field in the tissue may be perpendicular to the conductors. In other implementations, the antenna may induce a field in the tissue that is parallel to the antenna. In some implementations, the antenna may have a thickness of less than 5 millimeters and diameter of less than 9 centimeters or in other implementations, a length of less than 27 centimeters. The antenna may be incorporated into the circuit board 202. Likewise, the shape of the circuit board 202 and deflecting shield 218 may be altered to adapt the therapeutic device to particular applications. The thickness of the device is less than 10 millimeters and the area is less than 20 square centimeters. In one implementation, an adhesive material 216 such as a pharmaceutical adhesive may be mounted to the bottom layer under antenna 214 to adhere the device to bodily tissue. Other therapeutic delivery devices including a patch, a bandage, a pad, a brace, a strap, tape, adhesive and a cast also may be used. In some implementations, the components may be selected and arranged for specific applications. Referring to FIG. 6, for example, the therapeutic device 600 may have a generally annular shape in a therapeutic application such as post-operative healing over an eye or breast. In this case, the annular shape defines a hole 602 through which a patient may see while the device is in place.

Figure 3:
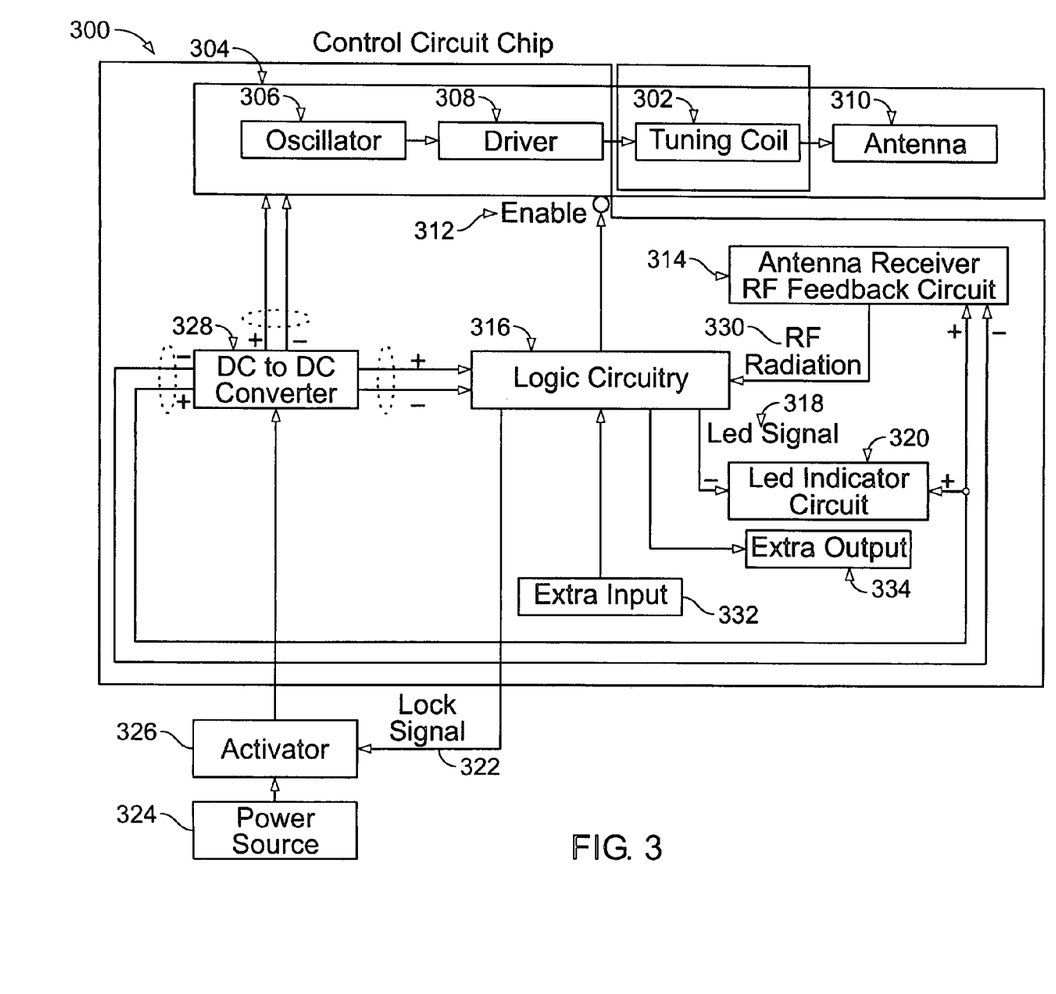
FIG. 3 is a block diagram of an implementation of a therapeutic electromagnetic device.

FIG. 3 is a block diagram of the circuitry of one implementation of a control circuit chip 300 used in a therapeutic electromagnetic device. Optionally, a tuning coil 302 may be included within the control circuit chip 300 or mounted separately. The components of the control circuit chip 300 may be integrated into one part or may be assembled from discrete components. The control circuit chip 300 includes an electromagnetic field generator 304 comprised of an oscillator 306 and a driver 308. Logic circuitry 316 coupled to the generator 304 provides an enable signal 312 to the generator 304. The logic circuitry also may provide an LED signal 318 to an indicator circuit 320, which, in turn, may be coupled to an indicator (not shown). Logic circuitry 316 may include discrete components, a programmable logic device (PLD), a microprocessor or other micro-controller unit (MCU). A power source 324 may be used to supply power to the electromagnetic therapy device. An activator 326 controls the flow of power from the power source to a DC to DC converter 328. The activator includes a switch that can provide for a one-time activation and then sustain activation for the duration of life of the power source. The DC to DC converter 328 provides power to the control chip components including the logic circuitry 316, the electromagnetic field generator 304 and an optional RF feedback circuit 314. The RF feedback circuit provides an RF radiation signal 330 to the logic circuitry 316. The logic circuitry also may provide an LED signal 318 to an LED indicator circuit and a lock signal 322 to the activator 326.

The electromagnetic field generator 304 comprises an oscillator 306 to generate an electromagnetic field, a driver circuit 308 to receive the electromagnetic field, amplify the wave and to provide the amplified wave to the optional tuning coil 302. The tuning coil 302 may be used to match the impedance of the driver 308 to an antenna 310, which is arranged to radiate the amplified electromagnetic energy. The oscillator 306 may be arranged to produce electromagnetic waves, including sinusoidal waves, at a carrier frequency of 27+/−0.5 megahertz (MHz). In an implementation, the electromagnetic therapeutic device has an average available power of less than approximately 1 milliwatt and a peak available radiated power density of less than 100 microwatts per square centimeter ($\mu W/cm^2$) measured substantially at the surface of the tissue. The electrical efficiency of average available radiated power generation also may be greater than 20%. Average available power is the power that the device can dissipate into a resistive load. The average available power is distinguished from the power of the carrier within each pulse, which is termed the "peak" power. The peak available radiated power density is the maximum carrier wave power as if it was continuous and not pulsed, but is divided by the loop area of the antenna. A high voltage generator (not shown) may be included to increase the intensity of the radiated field. The high voltage generator may produce less than 30 VDC and may be synchronized to allow energy transforming action between therapy pulses, so that therapy pulses are not affected by the energy transformation action. Energy transformation could comprise connecting the battery to an inductive coil for a brief duration, and then switching the coil into a diode or rectifier and capacitor. The capacitor accumulates charge at a higher voltage than the battery. When voltage on the capacitor reaches a predetermined value, the capacitor may be discharged into the frequency generator for producing a therapy pulse. Alternatively, a transformer connected to a rectifier and capacitor as a flyback transformer may replace the inductive coil.

The enable signal 312 may be used to initiate or curtail radiation of the electromagnetic energy. The RF feedback circuit 314 is arranged to detect RF radiation from the antenna 310 and to provide RF radiation signal 330 to logic circuitry 316. Based on the level of the RF radiation signal 330, the logic circuitry provides the LED signal 318 to enable/disable the LED indicator circuit 320, which drives the indicator (not shown) and provides an indication that the antenna is radiating electromagnetic energy. The logic circuitry 316, the LED indicator circuit 320 or the indicator may be arranged so that the indicator is either indicating continuously, intermittently or pulsating. The logic circuitry also may provide the enable signal 312 to enable/disable the electromagnetic field generator 304.

Figure 4A:
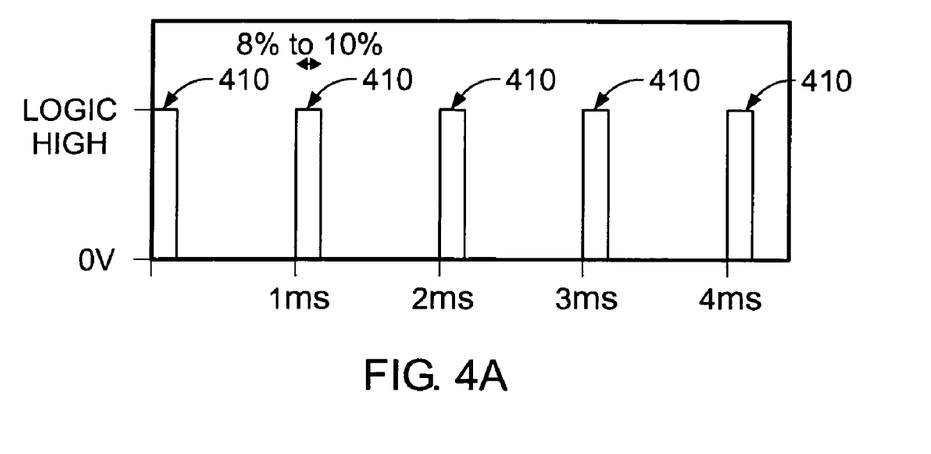
FIGS. 4A-B illustrate a control waveform and resulting RF waveform.
Figure 4B:
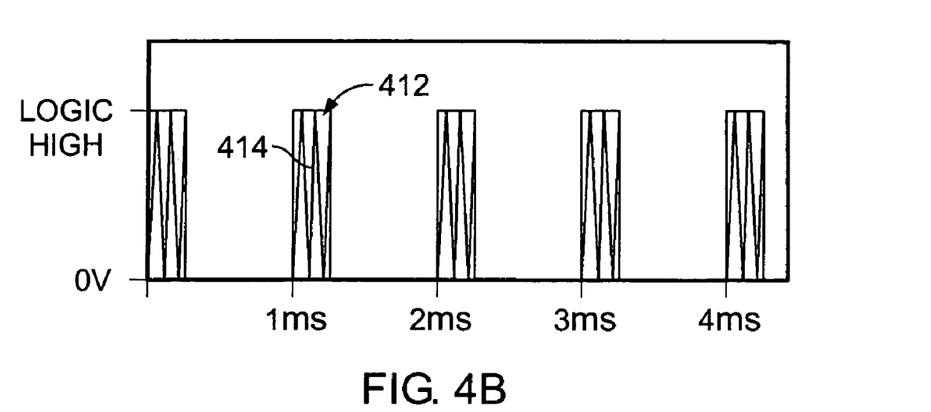
Figure 5A:
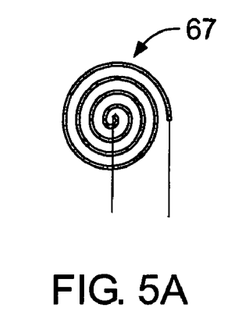
FIGS. 5A-I illustrate alternative antenna configurations.
Figure 5B:
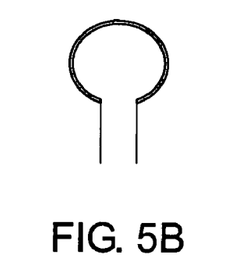
Figure 5C:
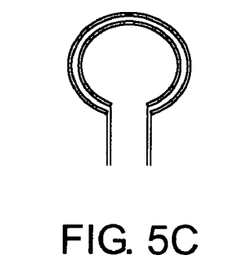
Figure 5D:
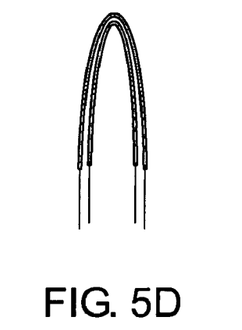
Figure 5E:
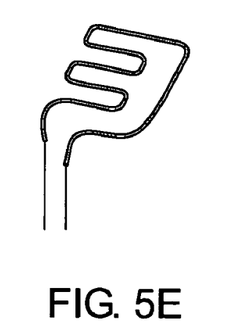
Figure 5F:
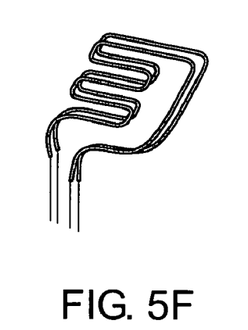
Figure 5G:
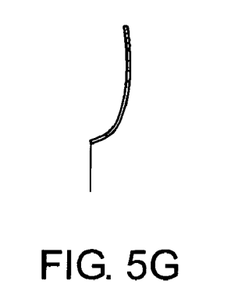
Figure 5H:
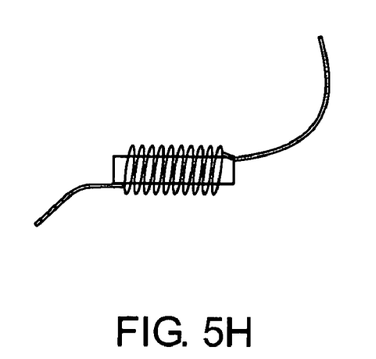
Figure 5I:
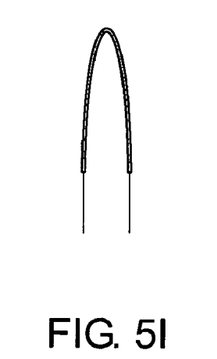

In an embodiment, the energy radiated by the antenna 310 may be pulsed. Pulsed electromagnetic field therapy (PEMF) may be used to provide electromagnetic field therapy over long periods of time and reduce heating of the bodily tissue. FIG. 4A illustrates that an enable signal 410 that may be provided from the logic circuit 316 to enable the generation and radiation of electromagnetic energy. In this example, the enable signal goes to a logic level high every millisecond. The enable pulse level is shown as a logic high but alternatively may be a logic low. In some implementations, the logic high level may be the power source, or regulated nonzero, voltage although other voltages are possible. The illustrated duty cycle is approximately 8% to 10%. In some implementations, the electromagnetic therapeutic device may operate in the frequency range of 3-30 MHz and application of the electromagnetic energy may be pulsed to maximize the therapeutic effect of the field. Pulses of 100 microsecond (μS) pulse duration at intervals of 1 millisecond (mS) (a pulse repetition rate of 1000 Hz) may be preferable. In order to reduce heating of the tissue, the electromagnetic field strength may be limited to less than 100 micro-Watts per square centimeter (μWcm-2) as measured proximate the surface of the tissue. FIG. 4B illustrates a resulting output 412 from the antenna. The electromagnetic field 414 is radiated from the antenna only when the enable signal 410 is at a logic high.

Referring again to FIG. 3, the power source 324 may be direct current (DC) and preferably less than approximately 10 VDC. The power source may be rechargeable. The rechargeable power source may be a battery of the lithium metal hydride or lithium ion or lithium polymer technology that may be recharged from an external source, including a sine wave field generator proximate the antenna 310 or separate coil (not shown) for the non-contacting induction of power from the external source into the therapeutic device. Current induced in the antenna or separate coil may be rectified and supplied as a reverse current to the rechargeable power source until the power source reaches a predetermined terminal voltage or case temperature.

The power source 324 is coupled to the activator 326. When the activator is actuated, power is coupled to the DC to DC converter which may boost and regulate the power source voltage level. Regulated output voltage from the DC to DC converter 328 is supplied to the logic circuitry 316, electromagnetic field generator 304 and RF feedback circuit 314. A lock signal 322 may be provided by the logic circuitry 316 to lock the activator in the "on" position when the activator is actuated at least once.

Optionally, extra input signals 332 and extra output signals 334 may be received and/or provided by the logic circuitry 316 for additional functionality. For example, an output signal may be provided that provides indicia of the level of the voltage level of the power source 324. The output signal may activate a visual or auditory alarm when the power source requires replacement. An output signal may be provided that provides indicia of a state of the bodily tissue. The electrical permittivity and conductivity of tissue affects the frequency of the carrier wave in the device. The ratio of conductivity ($\sigma$) to permittivity multiplied by angular frequency ($\omega\in$) determines the polarity of the frequency change. If $\sigma$ exceeds $\omega\in$ then the carrier frequency decreases. If $\omega\in$ exceeds $\sigma$ then the carrier frequency increases. As conductivity is related to pH and free ion concentration, while permittivity is related to abundance of polar molecules and cell membrane charge, the bioelectrical state of the tissue may be assessed by determining the carrier frequency change from that at initial application of the device.

Optionally, the extra output signal 334 may provide an enhanced electromagnetic field for directed movement of chemical or pharmaceutical molecules in tissue, such as silver ions for infection control. The enhanced electromagnetic field may be non-uniform in such a way as to direct movement of polar molecules, a method known as dielectrophoresis. Alternatively the enhanced electromagnetic field may induce an electric field which directs the movement of ions, a method known as iontophoresis.

An input 332 may be provided to receive external signals, for example, that alter the electromagnetic pulse duration, duty-cycle or pulse repetition rate of the electromagnetic field generated.

Figure 7A:
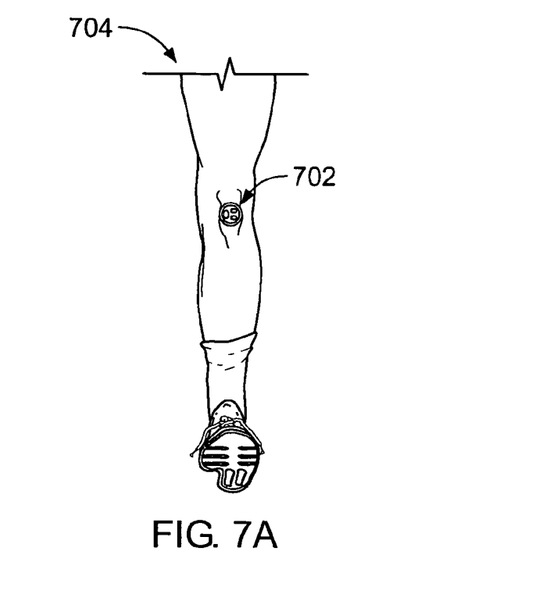
FIGS. 7A-D depict various applications of a therapeutic electromagnetic device.
Figure 7B:
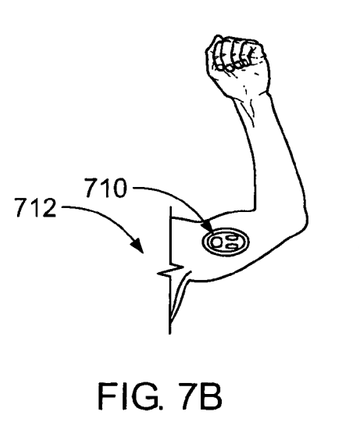
Figure 7C:
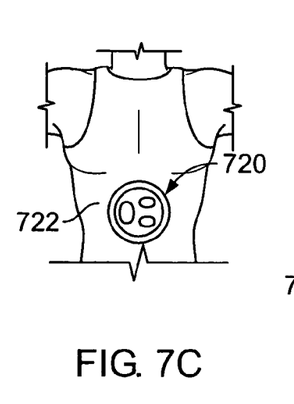
Figure 7D:
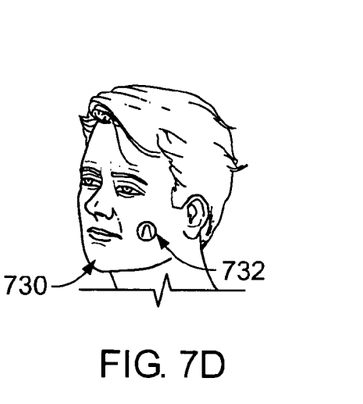

FIGS. 7A-D depict some applications of the therapeutic electromagnetic device. FIG. 7A depicts a therapeutic electromagnetic device affixed to a knee of a human leg 702. The device may be applied to aid in healing of, for example, a cracked knee, a cut, a sprain or strain. FIG. 7B depicts a therapeutic electromagnetic device 710 affixed to a muscle of a human arm 712 to aid in the healing of, for example, a sprain, a strain or a cut. FIG. 7C depicts a therapeutic electromagnetic device 720 affixed to a human stomach 722 where, for example, lipo-suction procedures were performed. FIG. 7D depicts a human face 730 where a therapeutic electromagnetic device 732 is affixed on a left side of the face to aid in healing of an injury such as a tooth cavity.

Method of Using Pulsed Electromagnetic Field (PEMF) Therapy in Certain Diseases

Bone and Joint Disorders: The urine of patients with bone and joint disorders typically shows elevated levels of hydroxyproline, hexosamine, creatinine, and uronic acid as a result of metabolic errors in connective tissues surrounding the affected site. Not only can these errors be corrected with PEMF therapy, but joint pain and swelling can be reduced and mobility of the joint increased. Another major advantage of PEMF therapy is that it significantly reduces the time required to heal fractured bones. It has also proven to be effective for osteomyelitis, osteoarthritis, rheumatoid arthritis, cervical spondylosis, and lower back pain (including that caused by disc displacement).

Diabetes Mellitus: Blood sugar levels may be slowly reduced to normal or near normal with application of a pulsed electromagnetic field (PEMF). Although the mechanism of action is not completely understood, the evidence obtained thus far indicates that the procedure not only increases the metabolism of glucose in the tissues but also increases the production of insulin and enhances insulin binding to its specific receptors. The therapy has also proven to be effective for gastritis, peptic ulcer, ulcerative colitis, irritable colon, and hemorrhoids.

Bronchial Asthma: Bronchiolar obstruction can be gradually reduced with PEMF treatment, which liquifies the mucous and facilitates spontaneous clearance. PEMF therapy also has anti-inflammatory action, which helps to ensure that the airways remain free and functional. In patients who have undergone the treatment, Forced Vital Capacity, Forced Expiratory Volume, and Peak Expiratory Flow Rates have increased and wheezing and dyspnea have significantly improved. The treatment is also effective for the common cold, tonsillitis, sinusitis, chronic bronchitis, bronchiectasis Cardiovascular Diseases: PEMF therapy is useful in the prevention of heart attacks in hypertensive patients. Treatment helps to lower blood cholesterol levels and increase the circulation of blood by centrally mediating vascular dilatation. This is particularly important in preventing platelet aggregation and maintaining adequate oxygenation and nutrition of cardiovascular and other tissues. PEMF therapy also effectively disintegrates atherosclerotic plaques. An additional advantage of the procedure is that it blocks the production of free radicals, which play a major role in cardiovascular damage at the cellular level. Other vascular conditions for which PEMF may be effective are phlebitis, endarteritis, and varicose vein.

Brain and Mind Disorders: Directed through the skull at different points, the PEMF can, by inductive coupling, produce an electric current in specific areas of the brain. It may thus be possible to enhance higher brain functions such as learning, memory, and creative thinking by selective stimulation of certain cells. PEMF may have broad application as the modality of choice for psychological disorders such as depression, aggression, anxiety, and stress as well as for Parkinson's disease, epilepsy, migraine, stroke, Alzheimer's and other degenerative brain disorders. In addition, cerebral palsy, mental retardation, hyperactivity, learning disabilities may be improved by PEMF stimulation of the central nervous system.

PEMF therapy can increase the efficiency of brain cells in synthesizing the neurochemicals required for the transmission of impulses or commands at the synaptic level and by improving the electrical activity of these cells. The brain is a neuro-chemical complex. The efficiency of the brain or intellectual capacity of the brain depends upon the efficient performance of the brain cells and production of the chemicals that are called neurotransmitters.

Too much dopamine can result in hyperactivity, while too little can result in uncoordinated movements of the limbs (Parkinsonism). Less acetylcholine, a neuro-chemical, in the brain is a reason for dementia especially of the Alzheimer's type. If the brain cells are stimulated repeatedly, after showing inhibition, they rebound and become more active than prior to stimulation. Since PEMF has the ability to stabilize the genes and prevent the activity of oxygen free radicals formed in the cells, it helps to retard the aging process.

Genitourinary Conditions: PEMF has been successfully used to treat genitourinary conditions such as menstrual irregularity, sterility, endometritis, and endometriosis in women and orchitis, prostatitis, and oligospermia in men.

Preoperative and Prophylactic Therapy: PEMF therapy over the epigastrium can provide increased blood perfusion to the body's extremities to reduce the inflammatory response to injury. Preoperative treatment of the surgical site has also been shown to accelerate healing.

Other implementations are within the scope of the following claims.

What is claimed is:

1. A therapeutic device comprising:
    an electromagnetic field generator;
    an antenna coupled to the generator and arranged to radiate the electromagnetic field;
    a deflecting shield for directing generated electromagnetic field energy toward a surface of bodily tissue of a patient;
    a battery power source coupled to the generator;
    an annular ring surrounding the battery and a wire wound around the annular ring; and
    an activator to initiate radiation of the electromagnetic field,
    wherein the therapeutic device is self-contained and portable and is adapted to be affixed to a patient and disposed over the surface of bodily tissue to induce an alternating current in the bodily tissue.

2. The therapeutic device of claim 1 wherein a peak available radiated power density is less than 100 microwatts per square centimeter measured substantially at the surface of the tissue.

3. A method comprising:
    providing a portable and disposable therapeutic device comprising a power source, an antenna, an annular ring to surround the power source, a wire wound around the annular ring, a deflecting shield; and an electromagnetic field generator;
    affixing the device to bodily tissue of a patient so that the patient can wear the device;
    causing the device to radiate an electromagnetic field, wherein the deflecting shield directs the radiated electromagnetic field into a bodily tissue; and
    inducing an alternating current in the bodily tissue, wherein the therapeutic device is self-contained and portable and is disposed over a surface of bodily tissue;
    wherein an average available radiated power is less than 1 milliwatt.

4. The method of claim 3 wherein an electrical efficiency of the average available radiated power generation is greater than 20%.

5. A method comprising:
    providing a portable and disposable therapeutic device comprising a power source, an antenna, an annular ring surrounding the power source, a wire wound around the annular ring, an electromagnetic field generator and a deflecting shield for directing an electromagnetic shield toward a surface of bodily tissue;
    affixing the device to bodily tissue of a patient so that the patient can wear the device;
    causing the device to radiate an electromagnetic field; and
    inducing an alternating current in the bodily tissue, wherein the therapeutic device is self-contained and portable and is disposed over the surface of bodily tissue;
    wherein a peak available radiated power density is less than 100 microwatts per square centimeter measured substantially at the surface of the tissue.

6. The method of claim 5 wherein affixing the device is done in such a way as to allow the patient to move about freely while the device is affixed.

7. The method of claim 6 further comprising inducing the alternating current in the bodily tissue with the affixed device as the patient moves about freely.

8. A therapeutic device comprising:
a circuit board;
a battery power source mounted atop the circuit board;
an electromagnetic field generator for generating an electromagnetic field, the electromagnetic field generator mounted atop the circuit board and electrically coupled to the power source;
a deflecting shield below the circuit board;
an antenna coupled to the electromagnetic field generator for radiating the electromagnetic field;
an annular ring surrounding the power source;
an adhesive material below the antenna to enable the therapeutic device to be adhered to bodily tissue of a patient; and
wherein the deflecting shield is positioned relative to the antenna so that the radiated electromagnetic field is directed into the bodily tissue of a patient.

9. The therapeutic device of claim 8 further comprising an activator atop the circuit board,
wherein the activator is coupled to the electromagnetic field generator to enable initiation of the radiation, and
wherein the activator is exposed for manipulation by the patient when the therapeutic device is adhered to the patient.

10. The therapeutic device of claim 8 wherein the therapeutic device is self-contained and portable.

11. The therapeutic device of claim 8 wherein an average available radiated power of the radiated electromagnetic energy is less than 1 milliwatt.

12. A therapeutic device comprising:
a circuit board;
a battery power source atop the circuit board;
an electromagnetic field generator coupled to the circuit board and comprising:
an oscillator; and
a driver coupled to the oscillator;
an antenna coupled to the electromagnetic field generator and adapted to radiate electromagnetic energy;
an activator coupled to the circuit board and exposed for manipulation by a patient to activate the electromagnetic field generator, wherein the electromagnetic field generator is electrically coupled to the power source through the activator;
an annular ring surrounding the battery power source having a wire wound around the annular ring;
a deflecting shield positioned relative to the antenna so that, during operation, some of the radiated electromagnetic energy from the antenna is directed by the deflecting shield away from the circuit board;
an adhesive material below the antenna to enable the therapeutic device to be adhered to the patient in such a manner that enables the patient to move about without restriction while the therapeutic device is adhered;
wherein the therapeutic device is self-contained and portable; and
wherein an average available power of the therapeutic device is less than approximately 1 milliwatt.

13. The therapeutic device of claim 12 wherein the electromagnetic field generator further comprises a tuning coil electrically coupled between the driver and the antenna, wherein the tuning coil is adapted to match the impedance of the driver to the impedance of the antenna.

14. The therapeutic device of claim 12 further comprising:
a light emitting diode coupled to the circuit board;
a feedback circuit arranged to detect the radiated electromagnetic energy; and
logic circuitry electrically coupled to the feedback circuit and to the light emitting diode, wherein the logic circuitry is adapted to enable or disable the light emitting diode, based on the detected radiated electromagnetic energy.

* * * * *